(12) United States Patent
Delovitch

(10) Patent No.: US 6,841,152 B1
(45) Date of Patent: Jan. 11, 2005

(54) METHODS FOR PROTECTING AGAINST AUTOIMMUNE DIABETES

(75) Inventor: Terry L. Delovitch, London (CA)

(73) Assignee: The Wellesley Hosp. Foundation, Toronto (CA)

( * ) Notice: Subject to any disclaimer, the term of this patent is extended or adjusted under 35 U.S.C. 154(b) by 0 days.

(21) Appl. No.: 09/341,407

(22) PCT Filed: Jan. 12, 1998

(86) PCT No.: PCT/CA98/00015
§ 371 (c)(1),
(2), (4) Date: Oct. 12, 1999

(87) PCT Pub. No.: WO98/30232
PCT Pub. Date: Jul. 16, 1998

(30) Foreign Application Priority Data

Jan. 10, 1997 (CA) ............................................. 2194814

(51) Int. Cl.[7] .......................................... A61K 39/395
(52) U.S. Cl. ............................... 424/130.1; 424/133.1; 424/141.1; 424/143.1; 424/144.1
(58) Field of Search .......................... 424/130.1, 133.1, 424/141.1, 143.1, 144.1, 137.1, 152.1, 153.1, 154.1; 530/387.1, 387.5, 388.1, 388.22, 388.7, 388.75; 514/866, 885

(56) References Cited

FOREIGN PATENT DOCUMENTS

| EP | WO9005541 A | 5/1990 |
|----|-------------|--------|
| EP | WO9200092   | 1/1992 |
| EP | WO9319767 A | 10/1993 |
| EP | WO9428912   | 12/1994 |
| EP | WO9503408 A | 2/1995 |
| EP | WO9505464 A | 2/1995 |
| EP | WO9614865   | 5/1996 |

OTHER PUBLICATIONS

Liang et al., J. Immunol. 1999; 163:2322–2329.*
Bowman et al. Immunology Today 15(3):115–120 1994.*
Shehadeh et al., "Effect of Adjuvant Therapy on Development of Diabetes in Mouse and Man," Lancet, 334:706–707 (1994).
Dahlquist et al., "The Cumulative Incidence of Childhood Diabetes Mellitus in Sweden Unaffected By BCG–Vaccination," Diabetologia, 38:873–874 (1995).
Sperling et al., "CD34 is A Murine T Cell Costimulatory Receptor That Functions Indepdently Of CD28," J. Exp. Med., 182:139–146 (1995).
Grewal et al., "Requirement For CD40 Ligand In Costimulation Induction, T Cell Activation, and Experimental Allergic Encephalomyelitis," Science, 273:1864–1867 (1996).
Wingren et al., "T Cell Activation Pathways: B7, LFA–3, and ICAM–1 Shape Unique T Cell Profiles," Critical Reviews In Immunology, 15(3&4):235–253 (1995).
Ekerfelt et al., "Transfer of myelin–specific cells deviated in vitro towards IL–4 production ameliorates ongoing experimental allergic neuritis," Clin. Exp. Immunol 123:112–118 (2001).

Karandikar et al. "Tissue–Specific Up–Regulation of B7–1 Expression and Function During the Course of Murine Relapsing Experimental Autoimmune Encephalomyelitis," The Journal of Immunology 161:192–199 (1998).
Saoudi et al. "TH2 activated cells prevent experimental autoimmune uveoretinitis, a TH1–dependant autoimmune disease," Eur. J. Immunol. 23:3096–3103 (1993).
Weintraub et al. "Up–Regulation and the Costimulatory Molecules B7–1 and B7–2 on Peripheral Lymphocytes in Autoimmune B6/gld Mice," The Journal of Immunology 159:4117–4126 (1997).
Yu et al. "Expression of GAD65 and Islet Cell Antibody (ICA512) Autoantibodies Among Cytoplasmic ICA+ Relatives is Associated with Eligibility for the Diabetes Prevention Trial–Type 1," Diabetes 50:1735–1740 (2001).
Arreaza et al., "Interleukin–4 Potential Immunoregulatory Agent in Therapy of Insulin–Dependent Diabetes Mellitus," Clin. Immunother. (4):251–260 (Oct. 1996).
Bendelac et al., "Syngeneic Transfer of Autoimmune Diabetes from Diabetic Nod Mice to Healthy Neonates," J. Exp. Med. (166):823–832 (Oct. 1987).
Berman et al., "Decreased IL–4 Production in New Onset Type I Insulin–Dependent Diabetes Mellitus[1]," J. Immunol. (157):4691–4696 (1996).
Bluestone, J.A., "New Perspectives of CD28–B7–Mediated T Cell Costimulation," Immunity (2):555–559 (Jun. 1995).
Cameron M.J. et al.: "Cytokline–and costimulation–mediated therapy of IDDM" Critical Reviews In Immunology 17(5–6):537–544 (1997).
Christianson et al., "Adoptive Transfer of Diabetes Into Immunodeficient NOD–scid/scid Mice," Diabetes (42):44–55 (Jan. 1993).
Corry et al., "Differential Effects of Blockade of CD28–B7 on the Development of Th1 or Th2 Effector Cells in Experimental Leishmaniasis[1], " J. Immunol. (153):4142–4148 (1994).
Freeman et al., "B7–1 and B7–2 Do Not Deliver Identical Costimulatory Signals, Since B7–2 but Not B7–1 Preferentially Costimulates the Initial Production of IL–4," Immunity (2):523–532 (May 1995).
Freeman et al., "Murine B7–2, an Alternative CTLA4 Counter–Receptor that Costimulates T Cell Proliferation and Interleukin 2 Production," J. Exp. Med. (178):2185–2192 (Dec. 1993).

(List continued on next page.)

*Primary Examiner*—Phillip Gambel
*Assistant Examiner*—Ilia Ouspenski
(74) *Attorney, Agent, or Firm*—Townsend and Townsend and Crew LLP

(57) ABSTRACT

Methods are provided for preventing the development of autoimmune diseases in susceptible subjects and for prolonging acceptance of tissue transplants by administration of an agonist of the T cell CD28 co-stimulatory receptor.

7 Claims, 8 Drawing Sheets

OTHER PUBLICATIONS

Haskins and McDuffie, "Acceleration of Diabetes in Young NOD Mice With a CD4+Islet–Specific T Cell Clone," *Science* (249):1433–1436 (Sep. 1990).

Jaramillo et al., "Insulin Dependent Diabetes Mellitus in the Non–Obese Diabetic Mouse: A Disease Mediated by T Cell Anergy?," *Life Sciences* (55):1163–1177 (Aug. 1994).

Jenkins et al., "Induction and Maintenance of Anergy in Mature T Cells," *Adv. Exp. Med. Biol.* (292):167–176 (1991).

Kalinski et al., "Functional Maturation of Human Naïve T Helper Cells in the Absence of Accessory Cells" *J. Immunol.* (154):3753–3760 (1995).

Katz et al., "T Helper Cell Subsets in Insulin–Dependent Diabetes," *Science* (268):1185–1188 (May, 1995).

Kawamura et al., "Comparative Analysis of B7–1 and B7–2 Expression in Langerhans Cells: Differential Regulation by T Helper Type 1 and T Helper Type 2 Cytokines," *Eur. J. Immunol* (25):1913–1917 (1995).

King et al., "CD28 Activation Promotes Th2 Subset Differentiation by Human CD4+," *Eur. J. Immunol.* (25):587–595 (1995).

Kuchroo et al., "B7–1 and B7–2 Costimulatory Molecules Activate Differentially the Th1/Th2 Developmental Pathways: Application to Autoimmune Disease Therapy," *Cell* (80):707–718 (Mar., 1995).

Lenschow D.J. et al: "DC28/B7 Regulation of Th1 and Th2 Subsets in the Development of Autoimmune Diabetes" *Immunity* 5(3):285–293 (1996).

Lenschow et al., "Differential Effects of Anti–B7–1 and Anti–B7–2 Monoclonal Antibody Treatment on the Development of Diabetes in the Nonobese Diabetic Mouse," *J. Exp. Med.*(181):1145–1155 (Mar. 1995).

Lenschow et al., "Expression and Functional Significance of an Additional Ligand for CTLA–4," *Proc. Natl. Acad. Sci. USA* (90):11054–11058 (Dec. 1993).

Liblau et al., "Th1 and Th2 CD4+ T Cells in the Pathogenesis of Organ–Specific Autoimmune Dieases" *Immunology Today* (16):34–38 (1995).

Linsley et al., "T–Cell Antigen CD28 Mediates Adhesion With B Cells By Interacting With Activation Antigen B7/BB–1," *Proc. Natl. Acad. Sci USA* (87):5031–5035 (Jul. 1990).

Lu et al., "CTLA–4 Ligands Are Required to Induce an In Vivo Interleukin 4 Response to a Gastointestinal Nematode Parasite," *J. Exp. Med.* (180):693–698 (Aug. 1994).

Mueller et al., "Pancreatic Expression of Interleukin–4 Abrogates Insulitis and Autoimmune Diabetes in Nonobese Diabetic (NOD) Mice,"*J. Exp. Med.* (184):1093–1099 (Sep. 1996).

Niklinska et al., "CD45 Tyrosine Phosphatase Activity and Membrane Anchoring Are Required for T–Cell Antigen Receptor Signaling," *Mol.Cell.Biol.*, (14):8078–8084 (1994).

Peach et al., "Complementarity Determining Region 1 (CDR1)–and CDR3–Analogous Regions in CTLA–4 and CD28 Determine the Binding to B7–1," *J. Exp. Med.* (180):2049–2058 (Dec. 1994).

Rabinovitch, "Immunoregulatory and Cytokine Imbalances in the Pathogenesis of IDDM," *Diabetes* (43):613–621 (May 1994).

Rapoport et al., "Interleukin 4 Reverses T Cell Proliferative Unresponsiveness and Prevents the Onset of Diabetes in Nonobese Diabetic Mice," *J. Exp. Med.* (178):87–99 (Jul. 1993).

Rohane et al., "Islet–Infiltrating Lymphocytes from Prediabetic NOD Mice Rapidly Transfer Diabetes to NOD–scid/scid Mice," *Diabetes* (44):550–554 (May 1995).

Seder et al., "CD28–Mediated Costimulation of Interleukin 2 (IL–2) Production Plays a Critical Role in T–Cell Priming for IL–4 and Interferon γ Production," *J. Exp. Med.* (179):299–304 (Jan. 1994).

Serreze et al., "Defects in the Differentiation and Function of Antigen Presenting Cells in NOD/Lt Mice[1]," *J. Immunol.* (150):2534–2540 (1993).

Shehadeh et al., "Altered Cytokline Activity in Adjuvant Inhibition of Autoimmune Diabetes," *J. Autoimmun.* (6):291–300 (1993).

Stack et al., "IL–4 Treatment of Small Splenic B Cells Induces Costimulatory Molecules B7–1 and B7–2[1]," *J. Immunol.* (152):5723–5733 (1994).

Thompson, "Distinct Roles for the Costimulatory Ligands B7–1 and B7–2 in T Helper Cell Differentiation," *Cell* (81):979–982 (Jun., 1995).

Wang et al., "The Role of CD4+ and CD8+ T Cells in the Destruction of Islet Grafts by Spontaneously Diabetic Mice," *Proc. Natl. Acad. Sci. USA* (88):527–532 (Jan. 1991).

Webb and Feldman, "Critical Role of CD28/B7 Costimulation in the Development of Human Th2 Cytokine–Producing Cells," *Blood* (86):3479–3486 (Nov., 1995).

Zipris et al., "Defective Thymic T Cell Activation by Concanavalin A and Anti–CD3 in Autoimmune Nonobese Diabetic Mice," *J. Immunol.* (146):3763–3771 (Jun., 1991).

* cited by examiner

METHODS FOR PROTECTING AGAINST AUTOIMMUNE DIABETES

This application claims priority under 35 U.S.C. §371 to PCT/CA98/00015.

This invention relates to methods and compositions for preventing the development of autoimmune disease in susceptible subjects. More particularly, the invention relates to treatment with an agonist of CD28 to prevent autoimmune disease development.

BACKGROUND OF THE INVENTION

Insulin-dependent diabetes mellitus (IDDM) or autoimmune diabetes is a polygenic, multifactorial, autoimmune disease heralded by T cell infiltration of the pancreatic islets of Langerhans (insulitis) and the β progressive T cell-mediated destruction of insulin-producing cells (Bach, 1994; Atkinson and Maclaren, 1994; Tisch and McDevitt, 1996).

Non-obese diabetic (NOD) mice are susceptible to the development of IDDM and are an accepted model for the development of autoimmune IDDM in humans.

$CD4^+$ T helper cells are required for the adoptive transfer of IDDM into recipient neonatal NOD mice or immunodeficient NOD.Scid mice (Bendelac et al., 1987, Christianson et al., 1993; Rohane et al., 1995). Cooperation between $CD4^+$ and $CD8^+$ T cells is required to initiate IDDM, and islet β cell destruction is $CD4^+$ T cell-dependent (Haskins and McDuffie, 1990; Wang et al., 1991). Current evidence suggests that the $CD4^+$ effector cells of IDDM in NOD mice at Th1 cells which secrete IL-2, IFN-γ and TNF-α and that the regulatory $CD4^+$ cells are Th2 cells which secrete IL-4, IL-5, IL-6, IL-10 and IL-13 (Rabinovitch, 1994; Liblau et al., 1995; Katz et al., 1995).

NOD mouse T cells show proliferative hyporesponsiveness to T cell receptor (TCR) stimulation and this hyporesponsiveness may be causal to the development of IDDM.

It has been shown that, beginning at 3–5 weeks of age, T cell receptor (TCR) ligation in NOD mice induces the proliferative hyporesponsiveness of NOD thymic and peripheral T cells, which is mediated by reduced IL-2 and IL-4 production (Zipris et al., 1991; Rapoport et al., 1993a; Jaramillo et al., 1994).

Decreased IL-4 production by human T cells from patients with new onset IDDM has also been demonstrated recently (Berman et al., 1996). Whereas addition of IL-4, a Th2-type cytokine, potentiates Il-2 production and completely restores NOD T cell proliferative responsiveness, addition of IL-2, a Th1-type cytokine, even at high concentrations, only partially restores NOD T cell responsiveness. These findings suggest that Th2 cells may be compromised in function to a greater extent than Th1 cells in NOD mice, and raise the possibility that Th2 cells require a higher threshold of activation than Th1 cells in these mice. IL-4 not only restores NOD T cell responsiveness in vitro, but prevents insulitis and IDDM when administered in vivo to prediabetic NOD mice (Rapoport et al., 1993a) or when transgenically expressed in pancreatic β cells (Mueller et al., 1996).

The proliferative hyporesponsiveness of regulatory Th2 cells in NOD mice may favour a Th1 cell-mediated environment in the pancreas of these mice, and lead to a loss of immunological tolerance to islet β cell autoantigens. This is consistent with the notion that restoration of the balance between Th1 and Th2 cell function may prevent IDDM (Rabinovitch, 1994; Liblau et al., 1995; Arreaza et al., 1996).

Optimal T cell activation requires signalling through the TCR and the T cell CD28 costimulatory receptor (CD28) (June et al., 1994; Bluestone, 1995; Thompson, 1995). Crosslinking of the TCR/CD3 complex in the absence of a CD28-mediated costimulatory signal induces a proliferative unresponsiveness that is mediated by the inability of T cells to produce IL-2 (Jenkins et al., 1991). CD28 costimulation prevents proliferative unresponsiveness in Th1 cells by augmenting the production of IL-2, which in turn promotes IL-4 secretion by T cells (Seder et al., 1994). The costimulatory pathway of T cell activation involves the interaction of CD28 with its ligands B7-1 and B7-2 on an antigen presenting cell (APC), with B7-2 considered as the primary ligand for CD28 (Linsley et al.,1990; Freeman et al., 1993; Lenschow et al., 1993; Freeman et al., 1995). When costimulation is blocked by either CTLA4-Ig or by anti-B7-1 or anti-B7-2 monoclonal antibodies (mAbs), differential effects on the incidence of various autoimmune diseases (e.g. IDDM) and on the development of Th1 and Th2 cells are observed (Kuchroo et al., 1995; Lenschow et al., 1995). Furthermore, in vivo studies have demonstrated that the generation of Th2 cells is more dependent upon the CD28-B7 pathway than the priming of Th1 cells, and suggest that the development of Th subsets in vivo may be influenced by limited CD28-B7 costimulation (Corry et al., 1994; Lu et al., 1994). Analyses of the development of human Th2 cells have yielded results similar to those observed in the mouse (King et al., 1995; Kalinski et al., 1995; Webb and Feldman, 1995). Interactions between CD28 and its B7-2 ligand are essential for the costimulation of an IL-4-dependent $CD4^+$ T cell response, and IL-4 increases B7-1 and B7-2 surface expression on certain professional APCs (eg. Langerhans cells) and B cells (Freeman et al., 1995; Kawamura et al., 1995; Stack et al., 1994). Thus, failure to activate NOD thymocytes and peripheral T cells sufficiently may be due to functional and/or differentiation defects in NOD APCs, which remain able to optimally activate islet β cell autoreactive $CD4^+$ effector T cells, but not regulatory $CD4^+$ T cells (Serreze et al., 1988; Serreze et al., 1993). Functional defects that compromise antigen presentation by NOD APCs, such as deficient CD28 costimulation, may lower their ability to stimulate regulatory Th2 cells without compromising their ability to stimulate autoreactive effector Th1 cells.

Proliferative hyporesponsiveness of T cells has been observed in other autoimmune diseases such as multiple sclerosis and myasthenia gravis.

If proliferative hyporesponsiveness of T cells in autoimmune disease could be overcome, it might be possible by that means to prevent the development of autoimmune diseases.

SUMMARY OF THE INVENTION

It has been shown that administration of an agonist of the T cell CD28 costimulatory receptor, referred to herein as CD28, can protect a susceptible subject from development of an autoimmune disease.

The treatment appears to stimulate the production of protective T cells in the treated subject.

The invention is illustrated by demonstration of the prevention of the development of autoimmune diabetes in the NOD mouse, an accepted model for human autoimmune diabetes.

In accordance with one embodiment of the invention, a method is provided for preventing the development of an autoimmune disease in a susceptible subject comprising administering to the subject an effective amount of a T cell CD28 costimulatory receptor (CD28) agonist.

In accordance with a further embodiment of the invention, a method is provided for prolonging acceptance of an engrafted tissue in a mammalian recipient of a tissue transplant comprising administering to the mammalian recipient an effective acceptance-prolonging amount of a CD28 agonist.

In accordance with a further embodiment of the invention, a pharmaceutical composition is provided for preventing the development of an autoimmune disease in a susceptible subject comprising an effective amount of a CD28 agonist.

In accordance with a further embodiment of the invention, a pharmaceutical composition is provided for prolonging acceptance of an engrafted tissue in a mammalian recipient of a tissue transplant comprising an effective amount of a CD28 agonist.

SUMMARY OF DRAWINGS

Certain embodiments of the invention are described, reference being made to the accompanying drawings, wherein.

Solid symbols: BALB/c mice

Open symbols: NOD mice

Figure 1:
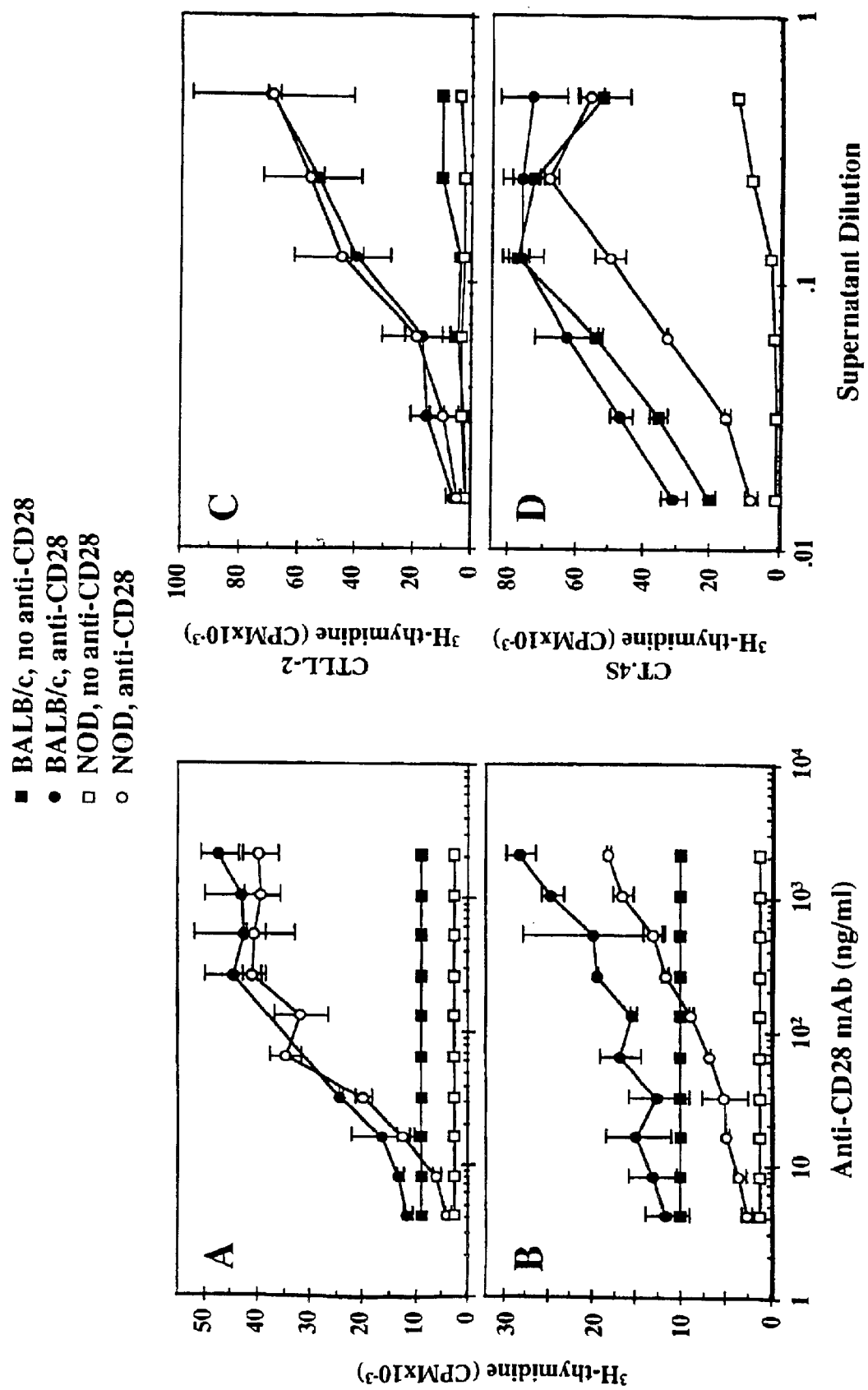
FIG. 1A shows thymocyte proliferation.
FIG. 1B shows splenic T cell proliferation, expressed as $^3$H thymidine incorporation in cpm, in the presence (circles) or absence (squares) of various concentrations of anti-CD28 monoclonal antibody.

FIG. 1C shows IL-2 production and FIG. 1D shows IL-4 production, expressed as $^3$H thymidine incorporation into CTLL-2 and CT.4S cells respectively, by NOD (open symbols) or BALB/c (solid symbols) thymocytes activated by anti-CD3 in the presence (circles) or absence (squares) of 1 µg/ml anti-CD28 MAb.

Figure 2:
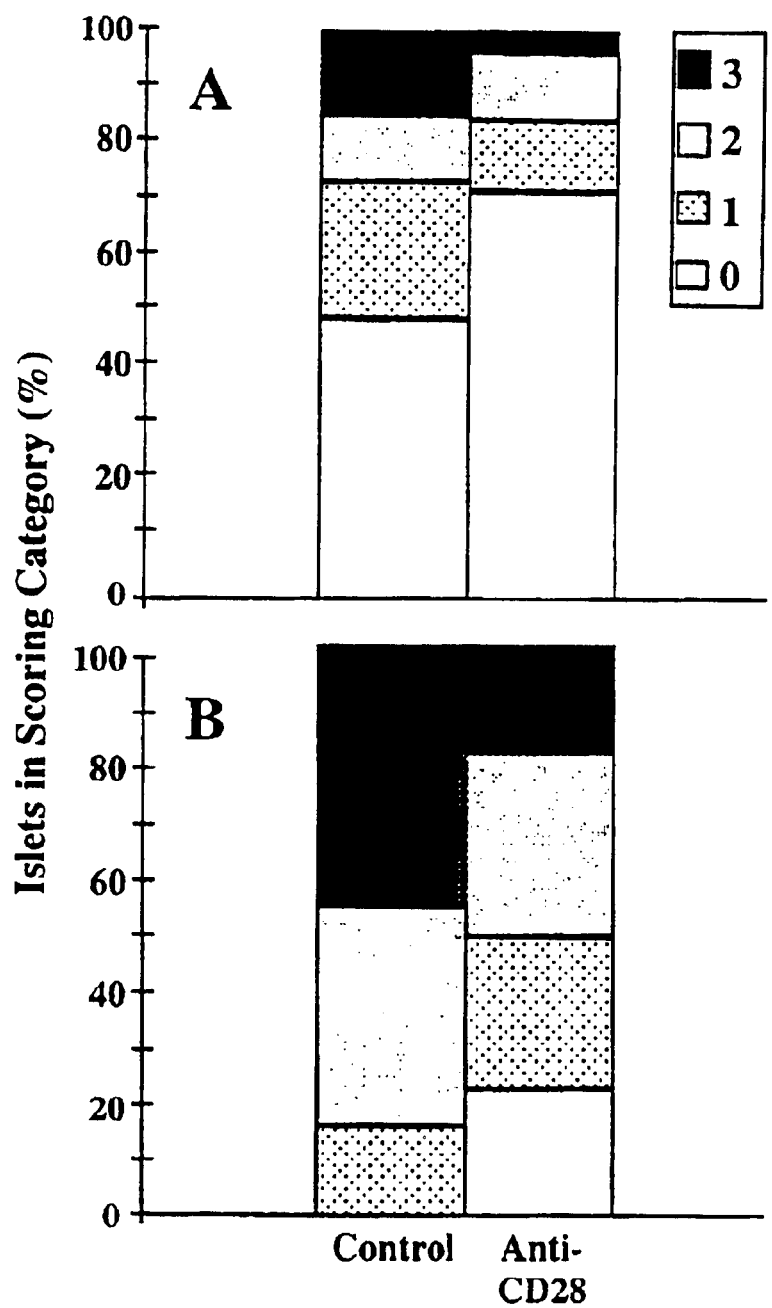

FIG. 2 shows insulitis scores in 8 week-old NOD mice (Panel A) and 25 week-old NOD mice (Panel B) treated with anti-CD28 antibody or hamster Ig (control).

FIG. 3A shows diabetes incidence (%) at various ages in NOD mice treated at age 2 to 4 weeks with anti-CD28 antibody (▲) or control hamster Ig (■).

FIG. 3B shows diabetes incidence (%) at various ages in NOD mice treated at age 5 to 7 weeks with anti-CD28 antibody (▲) or control hamster Ig (■).

Figure 4:
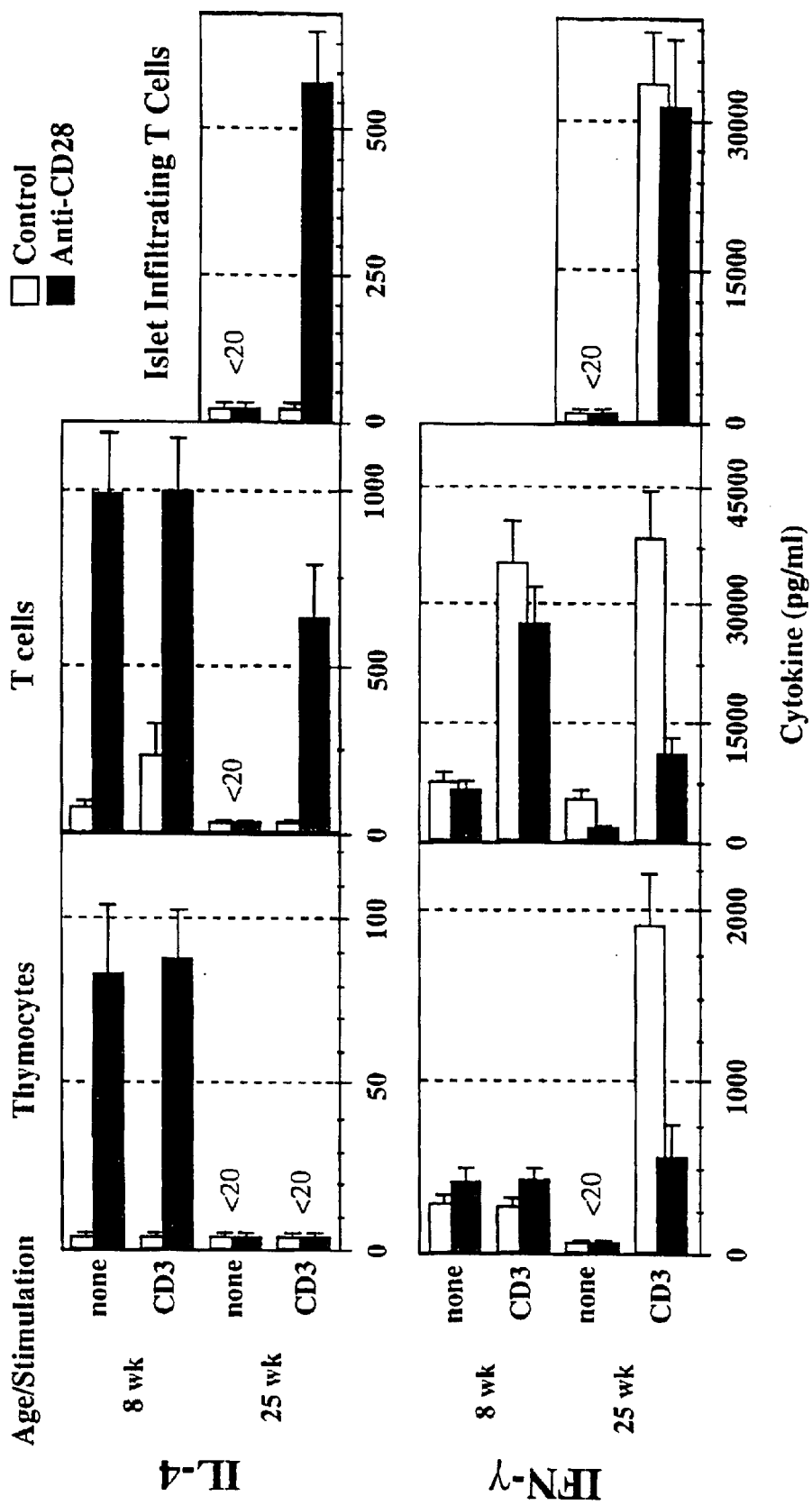

FIG. 4, upper panel, shows IL-4 production (pg/ml) by thymocytes, splenic T cells and islet infiltrating cells isolated from anti-CD28 antibody-treated (solid bars) or control (open bars) NOD mice (8 weeks or 25 weeks of age) in the presence or absence of 145-2C11 anti-CD3ε mAb.

FIG. 4, lower panel, shows IFN-γ production (pg/ml) by cells as described for FIG. 4, upper panel.

Figure 5:
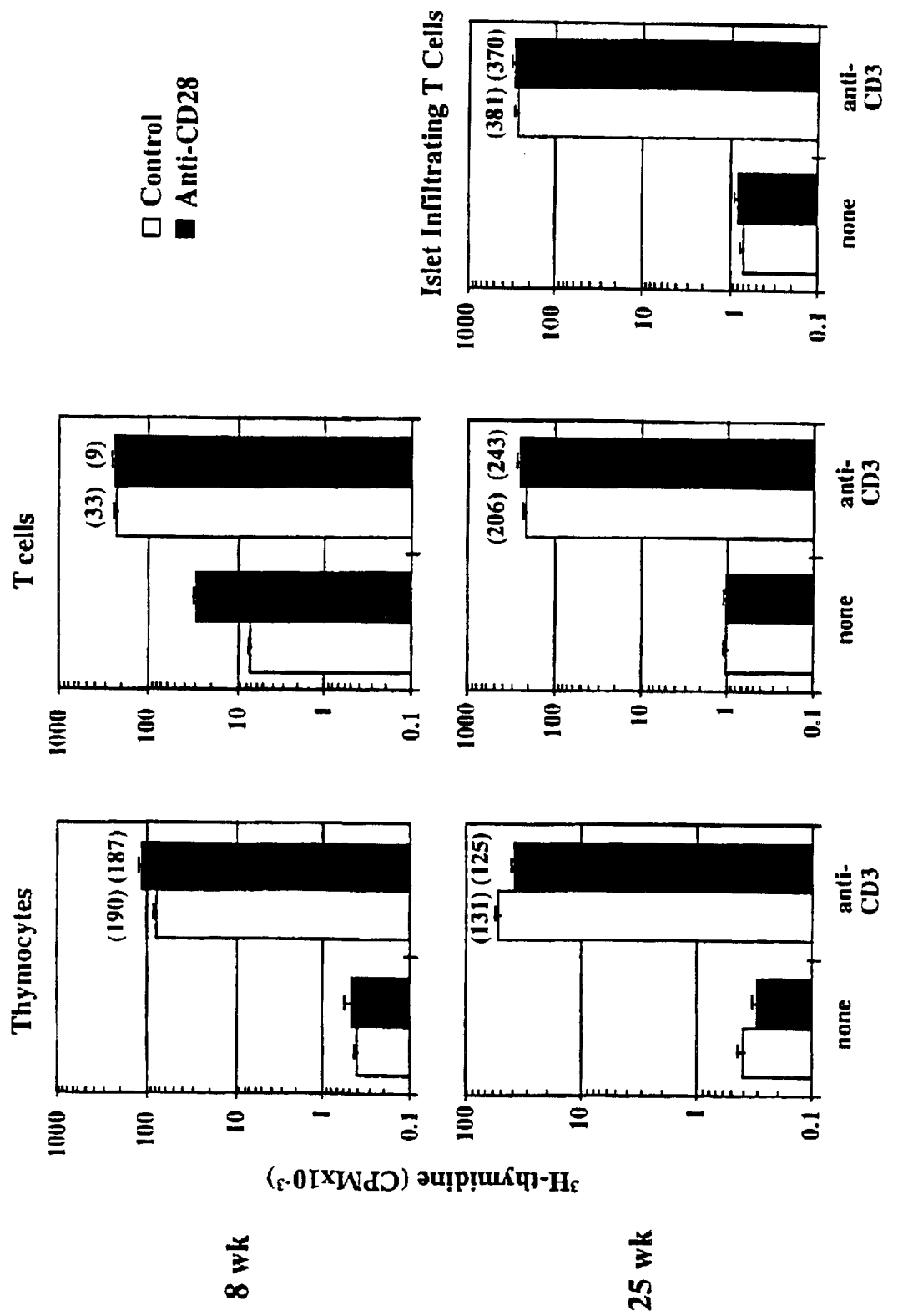

FIG. 5 shows proliferation (expressed as incorporation of $^3$H-thymidine in cpm×$10^{-3}$) of thymocytes, splenic T cells or islet infiltrating cells from 8- or 25-week old, anti-CD28 antibody-treated NOD mice, in response to anti-CD3ε antibody.

Stimulation indices (SI) were calculated as the ratio of average cpm of anti-CD3 stimulated cultures/average cpm of control cultures, and are shown in parentheses. Values (mean cpm±SD) shown are representative of three separate experiments.

Figure 6A:
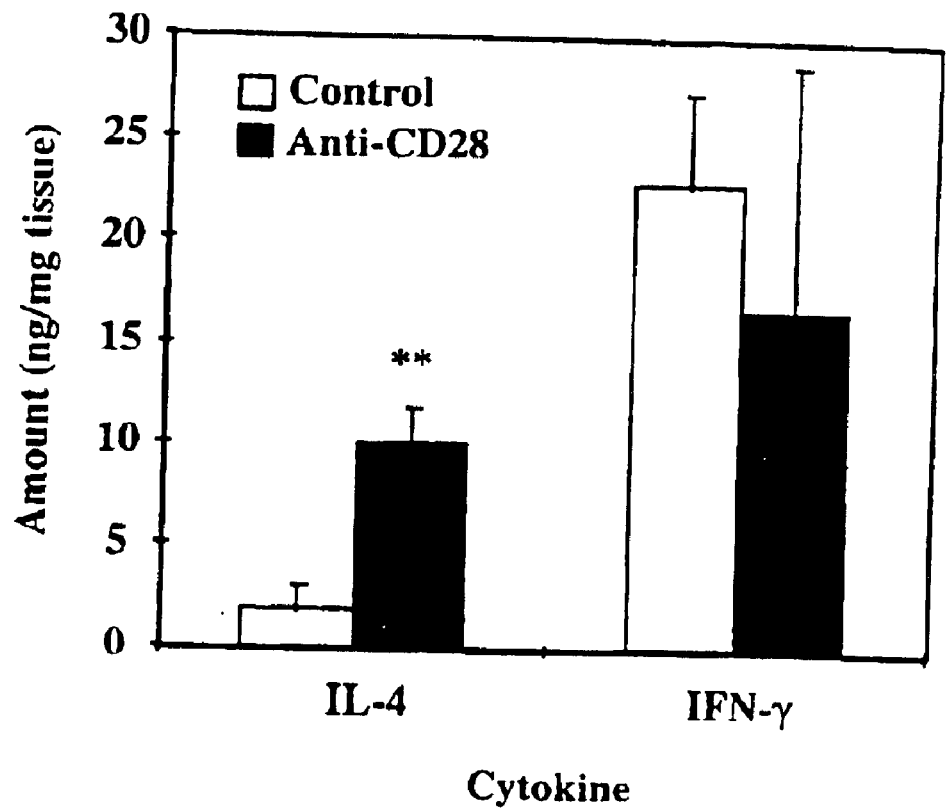

FIG. 6A shows pancreatic level of IL-4 and IFN-γ (ng cytokine/mg tissue) in NOD mice treated with anti-CD28 antibody (solid bars) or control hamster Ig (open bars).

Figure 6B:
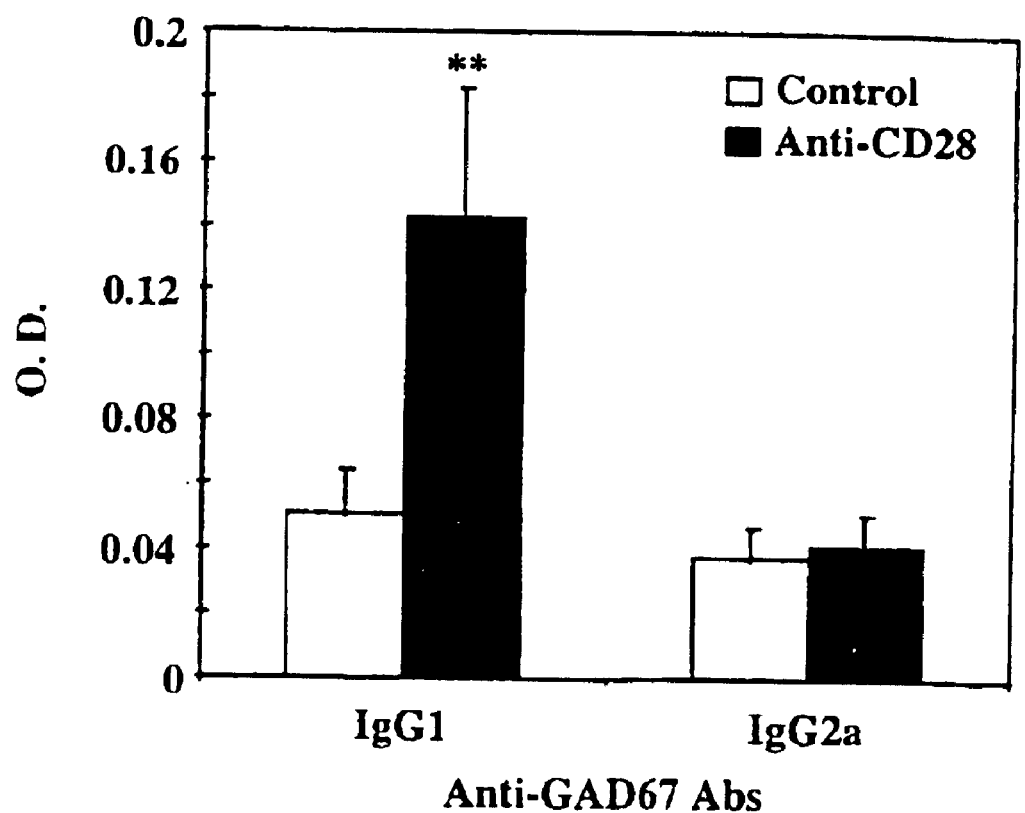

FIG. 6B shows serum levels of IgG1 and IgG2a isotype anti-GAD$_{67}$ antibodies in anti-CD28 antibody-treated NOD mice and controls.

Figure 7:
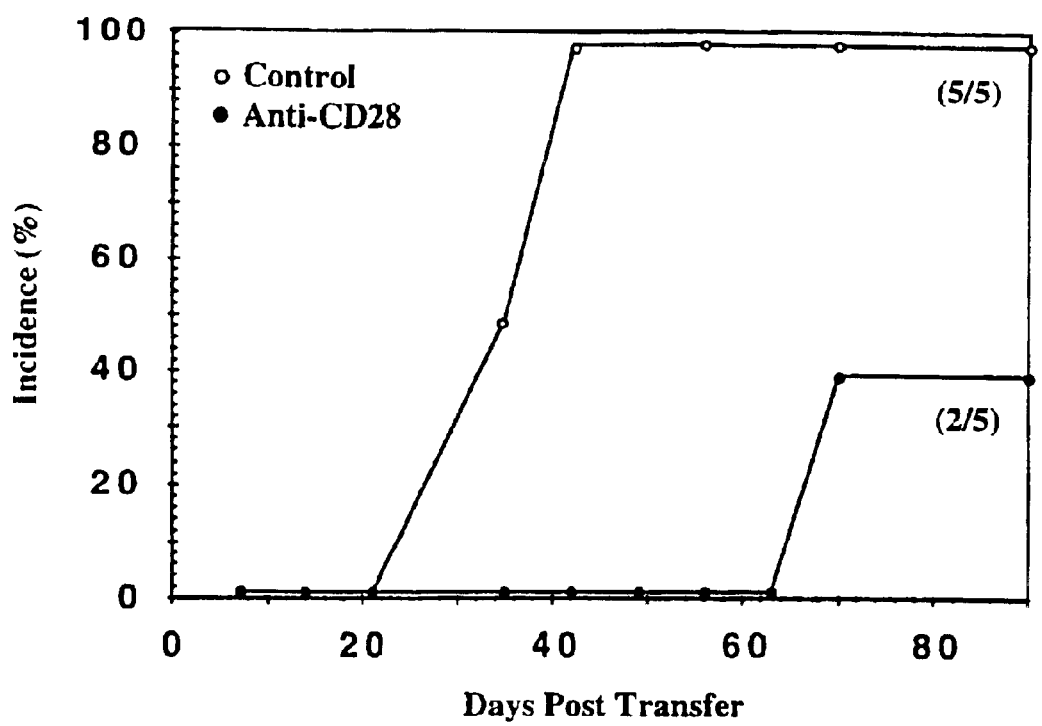

FIG. 7 shows the incidence of autoimmune diabetes in NOC.Scid mice injected with splenic T cells from anti-CD28 antibody-treated NOD mice (solid symbols) or control NOD mice (open symbols) at various times after injection (transfer) of splenic T cells.

DESCRIPTION OF THE INVENTION

The present invention provides a method for preventing the development of an autoimmune disease in a susceptible subject by treating the subject with an agonist of CD28.

Subjects susceptible to autoimmune diseases including autoimmune diabetes, multiple sclerosis, myasthenia gravis, rheumatoid arthritis, Hashimoto's thyroiditis, Sjogren syndrome and systemic lupus erythematosus may be treated by the method of the invention.

In accordance with a preferred embodiment, the method of the invention may be used to prevent the development of autoimmune diabetes in a susceptible human subject.

Suitable CD28 agonists include anti-CD28 agonist antibodies and B7-2 ligand protein extracellular domain polypeptide or effective fragments thereof.

B7-2 ligand protein is a transmembrane protein expressed on several types of haematopoietic cells, including antigen preventing cells and macrophages. The extracellular domain of B7-2 is involved in binding with CD28 (Peach et al., (1994), *J. Exp. Med.*, v. 180, pp. 2049–2058). Human B7-2 protein, a polypeptide corresponding to the extracellular domain of human B7-2, or an effective fragment thereof, may be used as a CD28 agonist in the method of the invention. An "effective fragment" is a fragment which acts as a CD28 agonist.

Fragments may be screened for CD28 agonist activity, for example, using the T cell proliferation assay described in Example 1.

Alternatively, B7-2 protein may be expressed recombinantly as a soluble B7-2 immunoglobulin fusion protein. For example, a fusion protein comprising human B7-2 protein fused to the Fc domain of human IgG1 may be prepared. DNA encoding B7-2 protein may be cloned by previously described methods (Linsley et al., (1993); Peach et al., (1994)).

In accordance with a preferred embodiment of the invention, development of an autoimmune disease is prevented by treating a susceptible subject with an anti-CD28 agonist antibody.

As will be understood by those skilled in the art, not all antibodies to CD28 may function as agonists to activate CD28. An "anti-CD28 agonist antibody" is an antibody which binds selectively to CD28 and whose binding leads to activation of CD28.

Anti-CD28 agonist antibodies may be raised against the full length CD28 protein or against portions of CD28 which contain epitopes involved in the binding of CD28. For example, antibodies may be raised to the complementarity determining region 1 (CDR1)- and CDR3-portions of CD28 which mediate the B7 ligand binding of CD28. The binding of CD28 is described in Peach et al. (supra), and Linsley et al., (1993), *Ann. Rev. Immunol.*, v. 11, pp. 191–212, the contents of which are incorporated herein by reference.

Anti-CD28 antibodies can readily be screened for CD28 agonist activity by a T cell proliferation assay, as described herein.

Human subjects susceptible to the development of autoimmune diabetes may be identified by screening based on a subject's HLA genetic make-up (Undlien et al., (1997))

or based on detection of predictive serum autoantibodies such as anti-insulin or anti-GAD antibodies (Verge et al., (1996)).

Treatment in accordance with the method of the invention should be administered in the neonatal period, from about 6 months to about 2 or 3 years of age. A series of treatments may be required over the 6 month to 2 year period of life.

Human subjects susceptible to other autoimmune diseases may be identified by screening tests appropriate for each disease, as is understood by those skilled in the art. For example, susceptibility to multiple sclerosis can be screened by MRI.

In accordance with a further embodiment, the invention provides pharmaceutical compositions for preventing the development of an autoimmune disease, the compositions comprising an effective amount of an agonist of CD28 and, optionally, a pharmaceutically acceptable carrier.

In accordance with a further embodiment, the invention provides a method for reducing the rejection of, and prolonging the acceptance of, an engrafted tissue in a mammal, by administering to the mammal an effective amount of a CD28 agonist. As used herein "engrafted tissue" includes allotransplants and xenotransplants of mammalian cells, tissues or organs. Transplantation of tissues or organs in humans is becoming ever more common, but there is always a need for control or suppression of the transplant recipient's immune system. Potential transplant recipients who may benefit from the method of the invention include recipients of kidney transplants, heart transplants, pancreas transplants, pancreatic islet transplants and liver transplants.

Treatment with the CD28 agonist may be, for example, by intravenous administration prior to, at the time of and after transplantation. For example, a suitable regime may be one treatment from one day to one week prior to transplant, one treatment on the day of the transplant and treatments at intervals of 2 to 4 days for as long as required after the transplant.

Dosage would be adjusted as required, in the judgment of the attending physician, but injections of 1 to 10 mg of agonist/kg body weight would be a suitable range for initial trial.

Antibodies

Polyclonal Antibodies

In order to prepare polyclonal antibodies, human CD28 co-receptor protein may be purified from T cells by conventional methods. The purified protein, coupled to a carrier protein if desired, is mixed with Freund's adjuvant and injected into rabbits or other suitable laboratory animals.

Alternatively, fusion proteins containing all or a portion of the CD28 co-receptor protein can be synthesised in a suitable host, such as a bacterium, by expression of an appropriate DNA sequence inserted in a suitable cloning vehicle. DNA encoding CD28 may be cloned by previously described methods (Linsley et al., (1993), *Ann. Rev. Immunol.*, v. 11, pp. 191–212; Peach et al., (1994), J. Exp. Med., v. 180, pp. 2049–2058).

Two widely used expression systems for producing recombinant fusion proteins in *E. coli* are glutathione-S-tranferase or maltose binding protein fusions using the pUR series of vectors and trpE fusions using the pATH vectors. Human CD28 may also be produced from CHO cells transfected with human CD28 cDNA.

The expressed CD28 protein can then be purified, coupled to a carrier protein if desired, and mixed with Freund's adjuvant (to help stimulate the antigenic response of the animal) and injected into rabbits or other appropriate laboratory animals. Alternatively, the protein can be isolated from CD28-expressing cultured cells. Following booster injections at weekly intervals, the rabbits or other laboratory animals are then bled and the sera isolated. The sera can be used directly or purified prior to use by various methods including affinity chromatography employing Protein A-Sepharose, antigen Sepharose or Anti-mouse-Ig-Sepharose.

Monoclonal Antibodies

Monoclonal anti-CD28 antibodies may also be produced by conventional methods after injecting into mice human CD28 co-receptor protein purified from T cells or produced by recombinant expression, or portions of CD28, as described above.

The protein is injected into mice in Freund's adjuvant, for example for nine times over a three week period. The mice spleens are removed and resuspended in phosphate buffered saline (PBS). The spleen cells serve as a source of lymphocytes, some of which are producing antibody of the appropriate specificity. These are then fused with a permanently growing myeloma partner cell, and the products of the fusion, hybridomas, are plated into a number of tissue culture wells in the presence of a selective agent such as HAT. The wells are then screened by ELISA to identify those containing cells making antibody specific for CD28. These cells are then plated and after a period of growth, these wells are again screened to identify antibody-producing cells. Several cloning procedures are carried out until over 90% of the wells contain single clones which are positive for antibody production. From this procedure a stable line of clones which produce the antibody is established. The monoclonal antibody can then be purified by affinity chromatography using Protein A Sepharose or ion-exchange chromatography, as well as variants and combinations of these techniques.

Alternatively, mice may be injected with human T cells, splenic lymphocytes are harvested and hybridomas prepared, screened and cloned as described above, to obtain hybridomas producing monoclonal antibodies specific for human CD28.

For example, mice may receive an initial injection of about $1-10 \times 10^6$ T cells in complete Freund's adjuvant, followed at weekly intervals for about 4 to 6 weeks with further injections of T cells in incomplete Freund's adjuvant, until high anti-CD28 serum antibody titers are detected.

Anti-CD28 antibodies with a binding affinity, Kd, of at least $10^{-8}$ are preferred and antibodies with $Kd \geq 10^{-9}$. are especially preferred.

In view of the high degree of conservation of amino acid sequence among mammalian CD28 proteins, anti-CD28 antibodies may also be raised against non-human CD28 (Linsley et al., supra; Peach et al., supra; June et al., (1994), *Immunol. Today*, v. 15, pp. 321–331).

Anti-CD28 antibodies are screened for CD28 agonist activity as described above.

Techniques are available and well known to those in the art to prepare humanised antibodies which have a variable region, specific for the CD28 co-receptor, synthesised in a non-human mammal, combined with a human constant region. Such humanised antibodies may be preferable for treatment of human subjects.

For example, the antibody may be genetically engineered to be a hamster/human chimeric monoclonal antibody of IgG1K isotype, the hamster constant regions being replaced with human counterparts while retaining the hamster antigen binding regions specific for human CD28, as described by Knight et al., (1993), *Mol. Immunol.*, v. 30, pp. 1443–1453. Portions of the antigen binding regions may also be genetically engineered to express the human counterpart antigen binding (Fv) regions.

Truncated versions of monoclonal antibodies may also be produced by recombinant techniques in which plasmids are generated which express the desired monoclonal antibody fragment(s) in a suitable host. Antibodies specific for mutagenic epitopes can also be generated.

Pharmaceutical Compositions

In a further embodiment, this invention provides pharmaceutical compositions for the prevention of autoimmune diseases in mammals.

Administration of a therapeutically active amount of a pharmaceutical composition of the present invention means an amount effective, at dosages and for periods of time necessary to achieve the desired result. This may also vary according to factors such as the autoimmune disease involved, the age, sex, and weight of the subject, and the ability of the CD28 agonist to elicit a desired response in the subject. Dosage regima may be adjusted to provide the optimum therapeutic response. For example, several divided doses may be administered daily or the dose may be proportionally reduced as indicated by the exigencies of the therapeutic situation.

By pharmaceutically acceptable carrier as used herein is meant one or more compatible solid or liquid delivery systems. Some examples of pharmaceutically acceptable carriers are sugars, starches, cellulose and its derivatives, powdered tragacanth, malt, gelatin, collagen, talc, stearic acids, magnesium stearate, calcium sulfate, vegetable oils, polyols, agar, alginic acids, pyrogen-free water, isotonic saline, phosphate buffer, and other suitable non-toxic substances used in pharmaceutical formulations. Other excipients such as wetting agents and lubricants, tableting agents, stabilizers, anti-oxidants and preservatives are also contemplated.

The compositions described herein can be prepared by known methods for the preparation of pharmaceutically acceptable compositions which can be administered to subjects, such that an effective quantity of the active substance is combined in a mixture with a pharmaceutically acceptable carrier. Suitable carriers and formulations adapted for particular modes of administration are described, for example, in Remington's Pharmaceutical Sciences (Remington's Pharmaceutical Sciences, Mack Publishing Company, Easton, Pa., USA 1985).

The CD28 agonist antibodies and proteins described herein may be sterilised by filtration and administered to a subject in need of treatment in a sterile saline solution.

The pharmaceutical compositions of the invention may be administered therapeutically by various routes such as by injection or by oral, nasal, buccal, rectal, vaginal, transdermal or ocular routes in a variety of formulations, as is known to those skilled in the art.

Administration by intravenous injection or infusion is preferred.

Optimal T cell activation requires signalling through both the TCR and the CD28 costimulatory receptors of the T cell. The T cells of NOD mice have been shown to be hyporesponsive to T cell receptor-stimulation of proliferation.

The present inventor has shown that this hyporesponsiveness of NOD T cells is associated with defective CD28 co-receptor costimulation.

It has been shown by the inventor that treatment of NOD mice with a CD28 agonist prevented the development of autoimmune diabetes. Treatment of neonatal NOD mice with an anti-CD28 antibody which gave CD28 costimulation completely restored the proliferative responsiveness of NOD thymocytes and peripheral T cells by augmenting their levels of secretion of IL-2 and IL-4. The stimulated increase in IL-4 secretion was predominant.

The antibody treatment effectively prevented the development of destructive insulitis in NOD mice and prevented the expected development of diabetes.

Treatment of neonatal NOD mice with anti-IL4 antibodies simultaneously with treatment with anti-CD28 antibodies abrogated the protective effect of the anti-CD28 antibodies against development of autoimmune diabetes.

The 37.51 anti-CD28 mAb used has been shown to block CD28/B7-1 interactions and thereby prevent tumour immunity (Allison, J. P. et al., *Curr. Opin. Immunol*, v. 7, pp. 682–686). Thus, this anti-CD28 mAb normally functions as an antagonist in animal model systems of tumour immunity. By contrast, in the NOD mouse model of IDDM, it has been demonstrated that the 37.51 anti-CD28 mAb acts as an agonist and activates rather than blocks CD28 signalling.

It is postulated that the antigen presenting cell (APC)-derived costimulatory signal transduced by the CD28 co-receptor on NOD mouse T cells may be insufficient to stimulate optimum T cell activation and that such CD28-signalled activation of IL-4-producing Th2 cells is necessary for protection from IDDM. The work of the inventor suggests that anti-CD28 antibody prevents IDDM in NOD mice by activating the CD28 signalling pathway in NOD T cells rather than by blocking the interaction between CD28 and its ligand, B7.

Prevention of IDDM by CD28 costimulation may be mediated by the activation of a subset of $CD4^+$ regulatory T cells that confer protection against IDDM. This subset of $CD4^+$ regulatory T cells may be hyporesponsive in NOD mice and may not receive a sufficient amount of the CD28/B7 costimulatory signal required for clonal expansion and effector function in NOD mice.

It has been proposed that precursor $CD4^+$ Th2 cells require a strong initial T-cell stimulation, and that the amount of IL-4 produced is proportional to the magnitude of the initial T cell stimulation. In the absence of CD28 costimulation, the production of IL-4 remains below the threshold required for the optimal development of Th2 cells (Seder and Paul, 1994; Thompson, 1995; Bluestone, 1995). It is of interest that B7-1 and B7-2 ligation of CD28 mediate distinct outcomes in $CD4^+$ T cells. B7-2 costimulation signals naive T cells to become IL-4-producing T cells, and thereby directs an immune response towards Th0 and Th2 cells (Freeman et al., 1995; Kuchroo et al., 1995). B7-1 costimulation seems to be a more neutral differentiative signal, and initiates the development of both Th1 and Th0/Th2 cells. Presumably, B7-2 plays a dominant role in the production of IL-4 due to its early expression during T cell activation (Freeman et al., 1995; Thompson, 1995). Thus, an insufficient or inappropriate signal resulting from a CD28/B7-2 interaction may be delivered to a subset of regulatory $CD4^+$ T cells in NOD mice, and this subset may not differentiate properly into functional IL-4 producing Th2 cells.

The inventor has examined whether anti-CD28 mAb treatment of NOD mice provides the costimulation required for the expansion of and cytokine production by regulatory IL-4 producing Th2-like cells. FIG. 4 shows that anti-CD3 stimulated (in vitro) NOD thymocytes obtained at 8 weeks, peripheral splenic T cells obtained at 8 weeks and 25 weeks and islet infiltrating T cells examined at 25 weeks of age produce significantly higher levels of IL-4 compared with the same subpopulations of cells isolated from control mice treated with a hamster Ig. Shortly after termination of treatment with anti-CD28 mAb, thymic and splenic T cells showed a higher basal (no stimulation) production of IL-4 compared to cells obtained from age-matched (8 week-old) control mice. With the exception of higher splenic T cell basal responses in 8 week-old mice, no differences were detected between the proliferative responses of thymocytes, splenic T cells and islet infiltrating cells from 8 and 25 week-old anti-CD28 treated NOD mice and those of the age matched controls (FIG. 5). The increase in basal T cell proliferation and IL-4 production may reflect the preferential costimulation of Th2 cells by anti-CD28 treatment in vivo. It has been found that anti-CD28 treatment in vivo leads to an increased production of IgG1 (which reflects increased IL-4 production by T cells) rather than IgG2a anti-GAD67 antibodies (FIG. 6B). Moreover, the total number of splenic lymphocytes was increased about 1.9-fold at 8 weeks of age and 1.7-fold at 25 weeks of age in anti-CD28 treated NOD mice relative to that of control treated mice (data not shown). These findings support the idea that anti-CD28 treatment elicits the expansion and survival of IL-4 producing Th2 cells in NOD mice.

Anti-CD28 treatment did not significantly alter the level of IFN-γ secretion by T cells from 8 week-old NOD mice compared with that observed in age-matched control mice. However, levels of IFN-γ secretion by thymocytes and splenic T cells from 25 week-old anti-CD28 treated NOD mice were markedly reduced in comparison to those levels detected in control mice. These data demonstrate the long term down regulation of Th1 cell function, which may arise from the preferential activation of Th2 cells induced by CD28 costimulation during the inductive phase of the autoimmune process. The downregulation and/or functional deviation of Th1 cells towards a Th2 cell phenotype by IL-4 is more effective than and dominant over the inhibition of Th2 cell function by IL-12 (Perez et al., 1995; Szabo et al., 1995; Murphy et al., 1996). These results also agree with reports that INF-γ secreting Th1 cells potentiate the effector phase of insulitis, IFN-γ is directly involved in α cell destruction (Pilstrom et al., 1995; Rabinovitch et al., 1995; Herold et al., 1996; Shimada et al., 1996) and the early differentiation of naive T cells into Th2 cells is dependent on CD28 signalling (Webb and Feldman, 1995; Lenschow et al., 1996). It is noteworthy that in human T cells, CD28 costimulation is a critical requirement for the development of Th2-like cells but not Th1-like cells, and Th2 cell function remains CD28-independent after the initial costimulation (Webb and Feldman, 1995).

Although anti-CD28 mAb treatment protects from IDDM, this treatment still allows for the development of a non-destructive insulitis. Therefore, this treatment does not interfere with the migration of diabetogenic T cells to the pancreatic islets. Rather, anti-CD28 treatment appears to induce regulatory T cells in the pancreas to suppress islet β cell destruction and progression to overt IDDM. Evidence in support of this is derived from assays of secretion of IL-4 and INF-γ by infiltrating cells from mice treated with anti-CD28 or control Ig (FIG. 4) and from analyses of the levels of expression of these cytokines in the pancreas of anti-CD28 treated NOD mice at 25 weeks of age (FIG. 6A). The intra-pancreatic expression of IL-4 was significantly higher in anti-CD28 mAb treated mice, whereas the expression of INF-γ remained essentially unaltered in these mice. Committed autoreactive cells, including Th1 cells, may accumulate in pancreatic islets but the functions of IL-4 predominate to inhibit INF-γ mediated β cell damage.

FACS analyses of the phenotype and surface expression of various cell adhesion molecules in anti-CD28 treated and control NOD mice at 8–25 weeks of age also indicated that anti-CD28 mAb treatment did not interfere with the migration of diabetogenic T cells to pancreatic islets (data not shown). The levels of surface expression of LFA-1, L-selectin and CD44 on the surface of splenic T cells did not suffer significantly between untreated and anti-CD28 treated NOD mice. Similarly, the levels of surface expression of markers of activation such as CD-69, ICAm-1 and B7-2 on B cells were increased only slightly in anti-CD28 treated NOD mice. The T (CD3$^+$):B (CD19$^+$) and CD4:CD8 T cell ratios in NOD mice were not altered by anti-CD28 treatment.

The activation of the CD4$^+$ Th2 cells may arise from the ability of CD28 ligation to sustain the proliferative response and enhance the longer term survival of T cells by the delivery of a signal that protects from apoptosis through the upregulation of survival factors such as Bcl-X$_L$.

EXAMPLES

The examples are described for the purposes of illustration and are not intended to limit the scope of the invention.

Methods of molecular genetics, protein and peptide biochemistry and immunology referred to but not explicitly described in this disclosure and examples are reported in the scientific literature and are well known to those skilled in the art.

Materials and Methods

Mice NOD/Del mouse colony was bred and maintained in a specific pathogen-free facility. Diabetes incidence among females in NOD colony was 40–50% at 15 weeks of age and 80–90% by 25 weeks. NOD-scid/scid mice generously provided by Dr. L. Shultz (The Jackson Laboratory, Bar Harbor, Me.) were bred in the colony and used as recipients in T cell transfer experiments. The age-and sex-matched BALB/c mice used as controls in the in vitro T cell proliferation experiments were also bred in the colony.

Anti-CD28 mAb Treatment

Either anti-CD28 mAb (50 μg), from supernatants from 37.51 hybridoma cells (provided by Dr. J. Allison, University of California, Berkeley, Calif.) secreting hamster anti-murine CD28 mAbs (Gross et al., 1992), purified by protein G affinity chromatography (Pharmacia Biotech, Uppsala, Sweden), or control hamster Ig (50 μg, Bio/Can Scientific, Mississauga, ON) was administered i.p. every other day to female NOD mice (n=20/group, randomized from 10 different litters) from 2- to 4-weeks of age. These mice were then boosted at 5, 7 and 8 weeks of age. Other groups of NOD mice (n=10/group, randomized from 5 different litters) received the same treatment starting at 5 weeks of age. Anti-CD28 monoclonal antibody is also available from Pharmingen, Catal. No. 01671D. Blood glucose levels (BGL) were measured weekly with a Glucometer Encore (Miles/Bayer, Toronto, ON). Animals with BGL>11.1 mmol/L (200 mg/dl) during two consecutive weeks were considered diabetic.

Histopathology Analysis

Mice were harvested periodically during the course of anti-CD28 or control Ig treatment, and pancreatic tissue was removed, fixed with 10% buffered formalin, embedded in paraffin and sectioned at 5 μm intervals. The incidence and severity of insulitis was examined by hematoxylin and eosin staining as well as insulin staining. A minimum of 20 islets from each mouse were observed, and the degree of mononuclear cell infiltration was scored by two independent, blinded observers using the following ranking: 0-normal, 1-peri-insulitis (mononuclear cells surrounding islets and ducts, but no infiltration of the islet architecture); 2-moderate insulitis (mononuclear cells infiltrating<50% of the islet architecture); and 3-severe insulitis (>50% of the islet tissue infiltrated by lymphocytes and/or loss of islet architecture). The immunohistochemical detection of insulin was performed using a porcine anti-insulin antibody (Dako Corp., Carpenteria, Calif.).

Cell Proliferation and Cytokine Secretion

Splenocytes and thymocytes from NOD or control mice were isolated as described in Rapoport et al., 1993. Splenic T cells were isolated on T cell columns (R & D Systems, Minneapolis, N) to a purity of $\geq 98\%$, as assayed by FACS analysis of CD3 cell surface expression. Cells ($10^6$/ml) were cultured in RPMI 1640 medium supplemented with 10% heat-inactivated FCS, 10 mM Hepes buffer, 1 mM sodium pyruvate, 2 mM L-glutamine, 100 U/ml penicillin, 0.1 mg/ml streptomycin, and 0.05 mM 2-ME (all purchased from Gibco Laboratories, Grand Island, N.Y.) with plate-bound 145-2C11 anti-CD3$\epsilon$ mAb (1/500 dilution of ascites; hybridoma kindly supplied by Dr. J. Bluestone, University of Chicago, Chicago, Ill.) in the presence or absence of various concentrations of the 37.51 anti-CD28 mAb. Cells were harvested after either 48 hr (splenocytes and T cells) or 72 hr (thymocytes), and were then assayed for the incorporation of [$^3$H]thymidine (1 $\mu$Ci/well; Amersham, Oakville, ON) added during the last 18 hr of culture.

Islet infiltrating cells were purified after isolation of pancreatic islets from collagenase P (Boehringer Mannheim, Laval, QC) digestion and centrifugation of the islets on a discontinuous Ficoll gradient. Free islets were hand-picked under a dissecting microscope to a purity of $\geq 95\%$, and purified islets were cultured for 24 hr to allow the emigration of lymphocytes from the islets. After culture harvest and isolation of viable lymphocytes by density gradient centrifugation on Lympholyte-M (Cedarlane Laboratories, Hornby, ON), the cells were cultured for 48 hr with anti-CD3$\epsilon$ as above. Culture supernatants were assayed for their concentration of cytokines by ELISA. IL-4 levels were interpolated from a standard curve using recombinant mouse (rm) IL-4 captured by the BVD4-1D11 mAb and detected by the biotinylated BVD6-24G2 mAb while INF-$\gamma$ concentrations were measured using rmINF-$\gamma$, the R4-6A2 mAb and biotinylated XMG1.2 mAb (all obtained from PharMingen, Mississauga, ON). Standard curves were linear in the range of 20–2000 pg/ml.

In some experiments, the relative levels of IL-2 and IL-4 secreted were quantified in a bioassay using the IL-2 dependent CTLL-2 T cell line (Gillis et al., 1977) and IL-4 dependent CT.4S T cell line (Li et al., 1989) (supplied by Dr. W. E. Paul, Laboratory of Immunology, National Institute of Allergy and Infectious Diseases, Bethesda, Md.). Two fold serial dilutions of test supernatants were added to CTLL-2 cells ($1.5 \times 10^4$) and Ct.4S cells ($5 \times 10^3$), which were cultured for 24 h and 48 h, respectively, in flat-bottomed 96 well-plates. Cell proliferation was assessed by addition of [$^3$H]-thymidine for 8 h prior to termination of culture, and [$^3$H]thymidine incorporation was determined as above.

Intrapancreatic Cytokine Analysis

Intrapancreatic IL-4 and INF-$\gamma$ concentrations in tissue samples were quantified, as described in Chensue et al., 1992; and Lukacs et al,. 1994. Briefly, pancreata were isolated and snap frozen in liquid nitrogen. Upon analysis, the samples were homogenized and sonicated in protease inhibitor buffered cocktail followed by filtration through 1.2 $\mu$m filters (Gelman Sciences, Ann Arbor, Mich.). The filtrates were analyzed for IL-4 and INF-$\gamma$ concentrations by ELISA, and the ELISA results were normalized relative to the total amount of protein per pancreas and recorded as ng/mg tissue.

GAD Antibody ELISAs

The presence of anti-GAD antibodies in collected sera was determined by ELISA as previously described (Elliott et al., 1994). Briefly, sera samples were added at appropriate dilutions to plates coated with murine $GAD_{67}$ (10 $\mu$g/ml). Using AP-conjugated goat anti-mouse isotype (IgG1 or IgG2a) antibodies with p-nitrophenylphosphate disodium in diethylamine buffer (substrate) the optical density was read at 405 $\mu$m to determine the relative amount of the individual anti-GAD isotype. All sera were titrated at 1:20, 1:40, 1:80, and 1:160 dilutions for anti-$GAD_{67}$ antibodies. Since no significant differences were found between the IgG1 and IgG2a ratio at the 1:20 dilution between treated and untreated mice, all sera were tested for the specific isotypes (IgG1 and IgG2a) at the 1:20 dilutions.

Adoptive Cell Transfer

Female NOD.Scid mice (n=5/group) 6 to 8 weeks of age were each injected i.p. with splenic T cells ($10^7$) from pre-diabetic female NOD mice previously treated with anti-CD28 mAb or control Ig. The recipients were followed for a maximum of 12 weeks after transfer and blood glucose levels (BGL) were monitored weekly.

Flow Cytometry

Splenic T cells and thymocytes ($10^5$) were suspended in 0.1% BSA and PBS/0.001% NaN3, and were then incubated for 30 min at 4° C. with various FITC- or PE-conjugated mAbs against different murine lymphocyte subpopulations and functional markers, including CD3, CD4, CD8, CD19, CD25, CD69, CD44, L-selectin, CD40, LFA1, B7-1 and B7-2 (PharMingen). Isotype matched (Ig) antibodies were used as negative controls. Cell fluorescence was analyzed using a FACScan and Lysis II software (both from Becton-Dickinson, San Jose, Calif.).

Example 1

Restoration of NOD T Cell Proliferative Responsiveness by CD28 Costimulation

Thymocytes and splenic T cells from 8 week-old NOD and control BALB/c mice were activated by plate-bound anti-CD3 in the absence or presence of varying dilutions (2 ng/ml–2 $\mu$g/ml) of soluble anti-CD28 mAb. Cell proliferation was determined by [$^3$H]thymidine incorporation. The results are shown in FIGS. 1A and 1B. The results of triplicate cultures are expressed as the mean values ± SD, and are representative of three different experiments.

FIG. 1A shows that CD28 costimulation provided by anti-CD28 markedly enhanced the anti-CD3-induced proliferative responses of NOD and BALB/c thymocytes, yielding 19.5- and 5.6-fold increases (at the highest concentration of anti-CD28) in these responses, respectively. Similar results were observed when an anti-TCR$\alpha\beta$ mAb was substituted for anti-CD3 (data not shown). However, when quiescent NOD and BALB/c thymocytes were stimulated by anti-CD28 in the absence of anti-CD3 (or anti-TCR$\alpha\beta$), a low level of proliferation was observed which was equivalent to the basal proliferative response detected in the absence of any stimulus (data not shown).

Anti-CD28 mAb also significantly enhanced the NOD, and to a lesser extent the BALB/c, anti-CD3-induced splenic T cell proliferative response (FIG. 1B). NOD and BALB/c splenic T cells were less responsive to CD28 costimulation (in terms of fold increases) than thymocytes from these mice, consistent with the notion that primed and naive T cells have different requirements for costimulation. Whereas primed splenic T cells require only TCR engagement to proliferate and produce IL-2, naive thymocytes require at least one additional costimulatory signal for optimal proliferation.

NOD and BALB/c thymocytes obtained from 8 week old mice were activated by plate bound anti-CD3 in the absence or presence of 1 µg/ml soluble anti-CD28 mAb (optimal concentration). Culture supernatants were removed, diluted and assayed for their IL-2 and IL-4 content by stimulation of proliferation of the CTLL-2 and CT.4S T cell lines, respectively. The results are shown in FIG. 1C and 1D. In FIG. 1C, the CTLL-2 cpm values of [$^3$H]thymidine incorporation for anti-CD3 activated NOD and BALC/c T cells represented by the highest supernatant dilution were 9,064±1,246 and 3,715±940, respectively. The results of triplicate cultures are expressed as the mean values ± SD, and are representative of four different experiments.

FIG. 1C demonstrates that anti-CD3 plus anti-CD28 costimulation significantly increased IL-2 production by both NOD (21.6-fold) and BALB/c (5.5-fold increase) but not BALB/c thymocytes (FIG. 1D). This may be attributable to the higher basal level of IL-4 production by BALB/c T cells than NOD T cells. CD28 costimulation augmented the proliferative responsiveness, as well as IL-2 and IL-4 production, of NOD thymocytes to levels comparable to those of BALB/c thymocytes. This may occur by a CD28-mediated pathway that significantly enhances the differentiation and ability of NOD thymocytes to produce IL-4, which can subsequently stimulate T cell proliferation in an autocrine and/or paracrine fashion. The finding that IL-4 restores the proliferative responsiveness of NOD thymocytes by increasing their level of IL-2 production agrees closely with the reported role for IL-4 in the stimulation of IL-2 production by mouse T cells in response to plate-bound anti-CD3.

The data above suggest that the induction of NOD T cell responsiveness is dependent largely on the ability of IL-4 to increase IL-2 production and stimulate NOD T cell proliferation. These results also suggest that both NOD Th1 and Th2 cell proliferative responsiveness can be restored by CD28-mediated costimulation via a mechanism that is partially, if not primarily, dependent on the enhancement of IL-2 and IL-4 production, respectively.

Example 2
Prevention of Insulitis by Anti-CD28 Antibody 8 week-old and 25 week-old NOD mice (n ≧5 in each group) were injected with either anti-CD28 mAb or control hamster Ig.

Following hematoxylin and eosin staining of pancreata, a minimum of 20 islets from each NOD mouse were observed and the degree of mononuclear cell infiltration was graded independently by two observers as follows: 0-normal; 1-peri-insulitis (mononuclear cells surrounding islets and ducts but not infiltrating the architecture); 2-moderate insulitis (mononuclear cells infiltrating<50% of the islet architecture); 3-severe insulitis (>50% of the islet tissue infiltrated by lymphocytes and/or loss of islet architecture).

Scores are shown in graphical form in FIG. 2.

Anti-CD28 treatment of NOD mice during the inductive phase (2–4 weeks of age) of development of IDDM prevented destructive insulitis. At 8 weeks of age, these anti-CD28 treated NOD mice had 70% of healthy islets (insulitis score=0) as seen in FIG. 2A.

At 25 weeks, in these anti-CD28 treated NOD mice (FIG. 2B), the percentage of islets displaying severe insulitis (insulitis score=3) was considerably lower (19%) than that observed in control treated mice (46%), and anti-CD28 treated animals still possessed 22% of normal healthy islets (insulitis score=0) while normal islets were not present in the control animals. In contrast, when anti-CD28 treatment was initiated after the onset of insulitis at 5 weeks of age, significantly less protection from insulitis was found (data not shown).

Example 3
Prevention of Autoimmune Diabetes in NOD Mice

Figure 3:
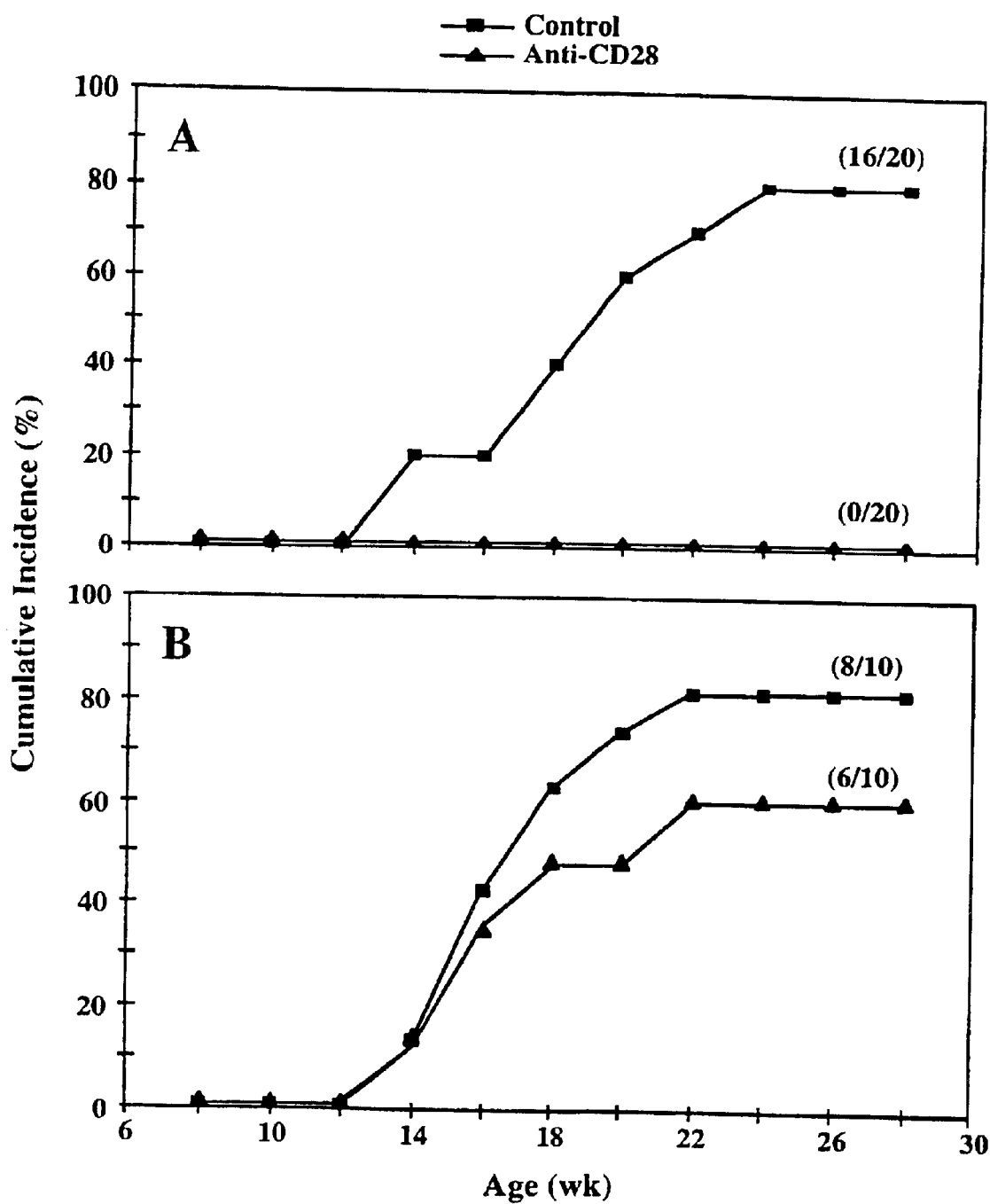

Twenty female NOD prediabetic mice (randomized from five different litters) were injected three times weekly from 2 to 4 weeks of age with 50 µg of either the 37.51 anti-CD28 mAb or control hamster Ig, and then boosted at 6, 7 and 8 weeks of age. Another group of ten females (randomized from three different litters) were similarly treated from 5 to 7 weeks of age. Mice were screened weekly for the presence of hyperglycemia (BGL>11.1 mmol/L) starting at 8 weeks of age. Diabetes was diagnosed when mice were hyperglycemic for two consecutive readings. The results are shown in FIG. 3.

Treatment of pre-diabetic NOD mice with anti-CD28 antibody at 2 to 4 weeks of age completely prevented the development of IDDM. At 28 weeks of age, 16 of 20 control mice had developed IDDM whereas none of 20 treated mice had developed IDDM (FIG. 3A). If anti-CD28 antibody treatment was delayed until after 5 weeks of age, significantly less protection against IDDM was obtained (FIG. 3B).

Anti-CD28 antibody treatment was unable to prevent cyclophosphamide-induced IDDM in NOD mice, regardless of whether cyclophosphamide was injected before or after anti-CD28 antibody administration (data not shown).

This results indicates that cyclophosphamide-sensitive regulatory T cells must be present and stimulated by anti-CD28 mAb in order to prevent IDDM by antibody treatment. Thus, CD28 costimulation represents a form of immunostimulation of NOD T cells which effectively protects against IDDM, particularly when anti-CD28 treatment is administered during the inductive phase of the disease.

Example 4
Induction of IL-4 Production in vivo by Anti-CD28 Antibody Treatment

Thymocytes, splenic T cells and islet infiltrating cells ($10^6$/ml) were pooled from at least 3 age-matched NOD mice at various times after treatment at 2–4 weeks with anti-CD28 mAb or control Ig, and were then stimulated with the 14.5-2C11 anti-CD3ε mAb (plate bound, 1/500 ascites dilution). After either 72 hr (thymocytes) or 48 hr (T cells and islet infiltrating cells) of culture, the concentration of IL-4 and INF-γ in cell supernatants from triplicate cultures were determined by ELISA. The results are shown in FIG. 4. Values shown are the mean ± SEM of three separate experiments.

Example 5
Lack of Enhancement of Anti-CD3-Stimulated T Cell Proliferation by Treatment with Anti-CD28 Antibody Thymocytes, splenic T cells and islet infiltrating cells ($2 \times 10^5$/well) from 8 and 25 week-old NOD mice (n≧3) injected at 2 to 4 weeks with either anti-CD28 mAb or control hamster Ig were cultured in triplicate wells in the presence or absence of the plate-bound 145-2C11 anti-CD3ε mAb (1/1000 ascites) for 48 hr (T cells, infiltrating cells) or 72 hr (thymocytes). Cell proliferation was determined by [$^3$H]thymidine incorporation. Results are shown in FIG. 5.

Example 6

Pancreatic IL-4 and INF-γ Enhancement by Anti-CD28 Antibody Treatment

NOD mice were treated with either anti-CD28 mAb (n=7) or control hamster Ig (n=5) at 2–4 weeks. Mice were sacrificed at 25 weeks of age, and intrapancreatic IL-4 and INF-γ concentrations were determined by ELISA. Results are shown in FIG. 6A. Values were expressed as mean ng cytokine/mg tissue. Comparison between means was performed by Student's t test, and a p value of <0.05 was chosen as the level of significance (**p<0.001).

Serum samples were assayed for anti-GAD antibodies as described above. Results are shown in FIG. 6B.

Example 7

Delay of IDDM Onset by T Cell Transfer

Splenic T cells ($10^7$) from 25 week-old, pre-diabetic female NOD mice previously untreated or treated at 2–4 weeks with anti-CD28 mAb were injected into 6–8 week-old female NOD.Scid mice (n=5/group). The recipient NOD-.Scid mice were followed for a maximum of 12 weeks after injection, and BGL were monitored weekly. Results are shown in FIG. 7.

When splenic T cells from non-diabetic NOD mice (25 weeks of age) were transferred into NOD.Scid recipients, the transfer of IDDM was either prevented or significantly delayed if recipient mice received T cells from anti-CD28 treated donors rather than T cells from control Ig treated mice (FIG. 7). All (5/5) of the mice injected with T cells from control Ig treated mice became diabetic between 35–40 days after transfer, while only 2/5 of the mice injected with T cells from anti-CD28 treated animals developed diabetes by 90 days post transfer.

The present invention is not limited to the features of the embodiments described herein, but includes all variations and modifications within the scope of the claims.

REFERENCES

Arreaza et al., 1996, *Clin. Immunother.*, v. 4, pp. 251–260;
Atkinson and Maclaren, 1994, *New Engl. J. Med.*, v. 331, pp. 1428–1436;
Bach, 1994, *Endocrine Rev.*, v. 15, pp. 516–542;
Bendelac et al., 1987, *J. Exp. Med.*, v. 166, pp. 823–832;
Berman et al., 1996, *J. Immunol.*, v. 157, pp. 4691–4696;
Bluestone, 1995, *Immunity*, v. 2, pp. 555–559;
Christianson et al., 1993, *Diabetes*, v. 42, pp. 44–55;
Corry et al., 1994, *J. Immunol.*, v. 153, pp. 4142–4148;
Elliott et al., 1994, *Diabetes*, v. 43, pp. 1494–1499;
Freeman et al., 1993, *J. Exp. Med.*, v. 178, pp. 2185–2192;
Freeman et al., 1995, *Immunity*, v. 2, pp. 523–532;
Gillis et al., 1977, *Nature*, v. 268, pp. 154–156;
Gross et al., 1992, *J. Immunol.*, v. 149, pp. 380–387;
Haskins and McDuffie, 1990, *Science*, v. 249, pp. 1433–1436;
Herold et al., 1996, *J. Immunol.*, v. 156, pp. 3521–3527;
Jaramillo et al., 1994, *Life Sciences*, v. 55, pp. 1163–1177;
Jenkins et al., 1991, *Adv. Exp. Med. Biol.*, v. 292, pp. 167–176;
Kalinski et al., 1995, *J. Immunol.*, v. 154, pp. 3753–3760;
Katz et al., 1995, *Science*, v. 268, pp. 1185–1188;
Kawamura et al., 1995, *Eur. J. Immunol.*, v. 25, pp. 1913–1917;
King et al., 1995, *Eur. J. Immunol.*, v. 25, pp. 587–595;
Kuchroo et al., 1995, *Cell*, v. 80, pp. 707–718;
Lenschow et al., 1993, *Proc. Natl. Acad. Sci USA*, V. 90, pp. 11054–11058;
Lenschow et al., 1995, *J. Exp. Med.*, v. 181, pp. 1145–1155;
Lenschow et al., 1996, *Immunity*, v. 5, pp. 285–293;
Li et al., 1989, *J. Immunol.*, v. 142, pp. 800–807;
Liblau et al., 1995, *Immunology Today*, v. 16, pp. 34–38;
Linsley et al., 1990, *Proc. Natl. Acad. Sci USA*, v. 87, pp. 5031–5035;
Lu et al., 1994, *J. Exp. Med.*, v. 180, pp. 693–698;
Mueller et al., 1996, *J. Exp. Med.*, v. 184, pp. 1093–1099;
Murphy et al., 1996, *J. Exp. Med.*, v. 183, pp. 901–913;
Peach et al., (1994), *J. Exp. Med.*, v. 180, pp. 2049–2058;
Perez et al., 1995, *Int. Immunol.*, v. 7, pp. 869–875;
Pilstrom et al., 1995, *Cytokine*, v. 7, pp. 806–814;
Rapoport et al., 1993a, *J. Exp. Med.*, v. 178, pp. 87–99;
Rabinovitch, 1994, *Diabetes*, v. 43, pp. 613–621;
Rabinovitch, 1995, *J. Immunol.*, v. 154, pp. 4874–4882;
Rohane et al., 1995, *Diabetes*, v. 44, pp. 550–554;
Seder and Paul, 1994, *Annu. Rev. Immunol.*, v. 12, pp. 635–673;
Seder et al., 1994, *J. Exp. Med.*, v. 179, pp. 299–304;
Serreze et al., 1988, *J. Immunol.*, v. 150, pp. 2534–2540;
Serreze et al., 1993, *J. Autoimmun.*, v. 6, pp. 291–300;
Shimada et al., 1996, *Diabetes*, v. 45, pp. 71–78;
Stack et al., 1994, *J. Immunol.*, v. 152, pp. 5723–5733;
Szabo et al., 1995, *Immunity*, v. 2, pp. 665–675;
Thompson, 1995, *Cell*, v. 81, pp. 979–982;
Tisch and McDevitt, 1996, *Proc. Natl. Acad Sci. USA*, v. 88, pp. 527–532;
Undlien et al., 1997, *Diabetes*, v. 46, pp. 143–149;
Verge et al., 1996, *Diabetes*, v. 45, pp. 926–933;
Wang et al., 1991, *Proc. Natl. Acad. Sci. USA*, v. 88, pp. 527–532;
Webb and Feldman, 1995, *Blood*, v. 86, pp. 3479–3486; and
Zipris et al., 1991, *J. Immunol.*, v. 146, pp. 3763–3771.

What is claimed is:

1. A method for protecting against the development of autoimmune diabetes in a susceptible subject comprising administering to the subject an effective amount of a T cell CD28 co-stimulatory receptor (CD28) agonist wherein the agonist is an anti-CD28 agonist antibody.

2. The method of claim 1 wherein the subject is a human subject.

3. The method of claim 2, wherein the antibody is a monoclonal antibody.

4. The method of claim 2 wherein the human subject is aged from about 6 months to about 2 or 3 years.

5. The method of claim 2 wherein the antibody is a humanized antibody.

6. The method of claim 2, wherein the antibody is a hamster/human chimeric antibody.

7. The method of claim 2, wherein the antibody is a polyclonal antibody.

* * * * *

UNITED STATES PATENT AND TRADEMARK OFFICE
CERTIFICATE OF CORRECTION

PATENT NO. : 6,841,152 B1
APPLICATION NO. : 09/341407
DATED : January 11, 2005
INVENTOR(S) : Terry L. Delovitch It is certified that error appears in the above-identified patent and that said Letters Patent is hereby corrected as shown below:

The assignee listed at item number (73) on the Title Page should be changed as follows:

"The Wellesley Hosp. Foundation"
""Toronto (CA)"

Should be removed, and replaced with

--John P. Robarts Research Institute--
--London (CA)--

Signed and Sealed this

Tenth Day of October, 2006

JON W. DUDAS
*Director of the United States Patent and Trademark Office*